(12) United States Patent
Bachovchin et al.

(10) Patent No.: US 6,966,186 B2
(45) Date of Patent: Nov. 22, 2005

(54) NON-CATALYTIC COMBUSTOR FOR REDUCING NOX EMISSIONS

(75) Inventors: Dennis M. Bachovchin, Delmont, PA (US); Thomas E. Lippert, Murrysville, PA (US)

(73) Assignee: Siemens Westinghouse Power Corporation, Orlando, FL (US)

( * ) Notice: Subject to any disclaimer, the term of this patent is extended or adjusted under 35 U.S.C. 154(b) by 135 days.

(21) Appl. No.: 10/426,728

(22) Filed: Apr. 30, 2003

(65) Prior Publication Data

US 2005/0188702 A1  Sep. 1, 2005

Related U.S. Application Data

(60) Provisional application No. 60/376,901, filed on May 1, 2002.

(51) Int. Cl.[7] .............................. F02C 3/14; F23R 3/02
(52) U.S. Cl. .......................... 60/722; 60/737; 431/215
(58) Field of Search .............................. 60/39.17, 39.22, 60/39.5, 39.511, 723, 731, 732, 733, 737, 60/738, 752, 722; 431/210–212, 215–217

(56) References Cited

U.S. PATENT DOCUMENTS

| | | | |
|---|---|---|---|
| 4,115,608 A | 9/1978 | Glass | |
| 4,240,784 A | 12/1980 | Dauvergne | |
| 4,870,824 A | 10/1989 | Young et al. | |
| 5,103,630 A * | 4/1992 | Correa | 60/39.17 |
| 5,263,325 A | 11/1993 | McVey et al. | |
| 5,339,634 A | 8/1994 | Gale et al. | |
| 6,082,111 A | 7/2000 | Stokes | |
| 6,101,814 A | 8/2000 | Hoke et al. | |
| 6,174,159 B1 | 1/2001 | Smith et al. | |
| 6,192,689 B1 | 2/2001 | Feitelberg et al. | |
| 6,286,298 B1 | 9/2001 | Burrus et al. | |
| 6,358,040 B1 | 3/2002 | Pfefferle et al. | |
| 6,829,896 B2 * | 12/2004 | Bruck et al. | 60/723 |
| 2004/0255588 A1 * | 12/2004 | Lundberg et al. | 60/723 |

FOREIGN PATENT DOCUMENTS

DE  39 03 687 A1  8/1989

* cited by examiner

Primary Examiner—Louis J. Casaregola

(57) ABSTRACT

A gas turbine engine combustor (26) including a primary combustion chamber (28), a mixer element (34), a mixing chamber (46) and a secondary combustion chamber (48). The primary combustion chamber receives a fuel oxidizer mixture flow (22) and discharges a partially oxidized mixture flow (32). The mixer element includes a plurality of flow channels (36, 38) for separating the partially oxidized mixture from a flow of an oxidizer (24) and producing a plurality of partially oxidized mixture flows interspersed with a plurality of oxidizer fluid flows. The mixer element may include a plurality of tubes (62) retained by an upstream tubesheet (70) and a downstream tubesheet (76). The mixer element may function as a heat exchanger to heat the oxidizer fluid flow and to cool the partially oxidized mixture flow upstream of the post-mixing chamber.

18 Claims, 2 Drawing Sheets

NON-CATALYTIC COMBUSTOR FOR REDUCING NOX EMISSIONS

This application claims priority to U.S. Patent Application Ser. No. 60/376,901, filed May 1, 2002.

FIELD OF THE INVENTION

This invention relates to combustors for gas turbines, and, in particular, to a non-catalytic combustor for reducing NOx emissions.

BACKGROUND OF THE INVENTION

Various combustor systems are well known in gas turbine applications to reduce the creation of pollutants in the combustion process. As known, gas turbines include a compressor for compressing air, a combustion stage for producing a hot gas by burning fuel in the presence of the compressed air produced by the compressor, and a turbine for expanding the hot gas to extract shaft power. The combustion process in many older gas turbine engines is dominated by diffusion flames burning at or near stoichiometric conditions with flame temperatures exceeding 3,000° F. Such combustion, however, typically produces a high level of oxides of nitrogen (NOx). Current emissions regulations have greatly reduced the allowable levels of NOx emissions.

One method for reducing combustion temperatures is to provide a lean, premixed fuel to the combustion stage. In a premixed combustion process, fuel and air are premixed in a premixing section of the combustor. Swirling may be induced to improve mixing as described in U.S. Pat. No. 6,082,111, and incorporated herein by reference. The fuel-air mixture is then introduced into a combustion stage where it is burned. Accordingly, local fuel-air ratios can be kept low enough so that flame temperatures are below those that produce substantial NOx emissions. However, the difficulty with lean, premixed combustion is that the lean flames may be unstable, and additional steps may be necessary to ensure that the flame remains stable.

One method of stabilizing a lean flame is to provide a stable, high temperature diffusion flame as a pilot flame to provide a constant source of ignition for the lean fuel-air mixture. A portion of the fuel and air supplied to the combustor is reserved to provide for the pilot flame. However, a diffusion flame is a source of NOx and, consequently, the size of the pilot flame must be minimized, such as by premixing the fuel and air provided to the pilot flame, to decrease NOx emission. In addition to pilot flame optimization, the degree of mixing of the fuel and air can minimize formation of NOx pollutants. This approach can produce NOx levels as low as 6 to 9 parts per million (ppm) if well engineered, but stability of the lean flame is still a concern.

Another method to reduce NOx emissions is to use a Rich-Quench-Lean (RQL) technique, wherein a rich fuel air mixture is ignited and partially combusted before being quickly diluted with an injection of air to create a lean mixture. However, it is difficult to achieve rapid, uniform mixing of the injected air with the partially combusted rich fuel air mixture to quickly drive the overall mixture to a lean state while avoiding high temperature quasi-diffusion flame zones.

In yet another method to reduce NOx emissions, catalytic combustion can be used to stabilize the lean premixed flame instead of using a pilot flame. In one approach, the bulk lean mixture can be passed through a catalyst combustor section wherein a catalytic material (for example, a noble metal such as platinum or palladium) is adhered to a metal substrate. In this lean catalytic approach, the mixture is partially converted before exiting the catalytic section and is raised in temperature so that the catalyzed mixture burns stably downstream. The problem with this approach is that the lean mixture must be somewhat preheated (a step that generates NOx emissions) to be ignited by the catalyst, and it is possible to allow the catalytic reaction to proceed too far, thus exposing the catalyst to damaging temperatures. In addition, the catalytic combustor section is expensive and requires increased servicing and replacement. If well engineered, this approach can produce NOx levels as low as 2 to 4 ppm, but optimal mixing is required.

Yet another method to reduce NOx emissions is to pass a rich reactive mixture of the fuel and a relatively small portion of air over a set of catalyst coated tubes or plates to form a high temperature fuel gas. Such a system is described in U.S. Pat. No. 6,415,608, owned by the assignee of the current invention and incorporated herein by reference. The coated tubes or plates are cooled by a remaining larger portion of the air provided to the combustor by passing the larger portion of air over the non-catalytic backsides of the tubes or plates in a "backside cooling" configuration. This technique has advantages over the lean catalytic method because the catalyst is less prone to overheating, and no preheating of the fuel-air mixture is required. By nature of the tube discharge configuration, this technique provides enhanced premixing of the high temperature fuel gas and the larger portion of the air in a downstream homogenous burnout zone. This approach can produce NOx levels as low as 1 to 3 ppm, if well engineered.

There is an ongoing need for improved combustion techniques to provide low NOx emissions and stable combustion conditions.

SUMMARY OF THE INVENTION

A combustor is described herein as including: a primary combustion chamber receiving a first fuel-oxidizer mixture and discharging a partially oxidized mixture; a mixer element receiving the partially oxidized mixture and a flow of an oxidizer into a plurality of separate flow channels and comprising a plurality of outlet ends discharging the partially oxidized mixture interspersed among a plurality of outlet ends discharging the oxidizer; and a chamber in fluid communication with the outlet ends of the mixer element for mixing the partially oxidized mixture with the oxidizer downstream of the mixer element.

The combustor may further include a heat exchanger having a shell for receiving the partially oxidized mixture, a plurality of tubes for receiving a flow of an oxidizer, and a plurality of outlet ends discharging the partially oxidized mixture interspersed among a plurality of outlet ends discharging the oxidizer; a tubesheet at a downstream end of the tubes; a tubesheet at an upstream end of the tubes; a mixing chamber in fluid communication with the outlet ends of the heat exchanger for further mixing the partially oxidized mixture with the oxidizer downstream of the mixer element; and a secondary combustion chamber for further combusting the partially oxidized mixture with the oxidizer downstream of the post mixing chamber.

A method of combusting a fuel-oxidizer mixture is described herein as including: partially combusting a fuel-oxidizer mixture in a combustion chamber to create a partially oxidized mixture; providing an oxidizer fluid; delivering the partially oxidized mixture and the oxidizer fluid to a mixer element comprising a plurality of flow channels for producing a plurality of partially oxidized mixture flows interspersed among a plurality of oxidizer fluid flows; mixing the partially oxidized mixture flows with the oxidizer fluid flows downstream of the mixer element; and further combusting the partially oxidized mixture flows with the oxidizer fluid flows.

BRIEF DESCRIPTION OF THE DRAWINGS

These and other advantages of the invention will be more apparent from the following description in view of the drawings that show.

DETAILED DESCRIPTION OF THE INVENTION

Figures 1, 4:
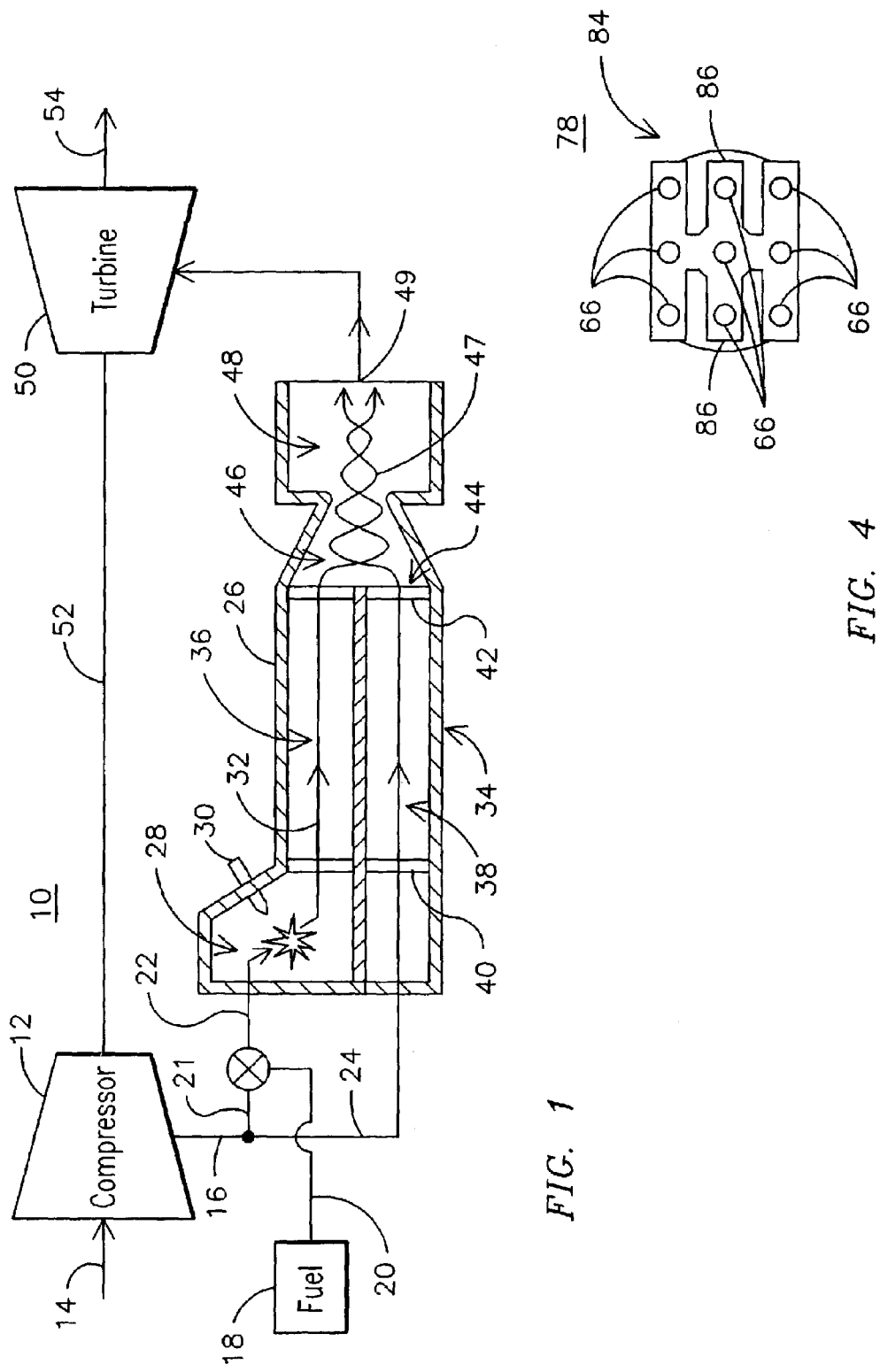
FIG. 1 is a functional diagram of a gas turbine engine having an improved combustor design.
FIG. 4 is a sectional view of the manifold of the tubesheet of FIG. 3 indicated by the section arrows labeled "4—4" in FIG. 3, showing aspects of the interior thereof.

FIG. 1 illustrates a gas turbine engine 10 having a compressor 12 for receiving a flow of filtered ambient air 14 and for producing a flow of compressed air 16. The compressed air 16 is separated into a fuel mixing flow 21 and an oxidizer flow 24, respectively, for introduction into a combustor 26. The fuel mixing flow 21 is mixed with a flow of a combustible fuel 20, such as natural gas or fuel oil for example, provided by a fuel source 18, to create a fuel-rich fuel-oxidizer mixture flow 22 prior to introduction into a primary combustion chamber 28 of the combustor 26. In the primary combustion chamber 28, the fuel-oxidizer mixture flow 22 may be ignited by igniter 30 to form a partially oxidized mixture flow 32. From the primary combustion chamber 28, the partially oxidized mixture flow 32 is directed into a partially oxidized mixture flow channel 36 of a mixer element 34. The oxidizer flow 24 is directed into an oxidizer flow channel 38 of the mixer element 34 so that the mixer element 34 separates the partially oxidized mixture flow 32 from the oxidizer flow 24 as the respective flows 24, 32 move through the respective flow channels 36, 38. Advantageously, the mixing element 34 provides improved mixing of the respective flows at an outlet 44 of the mixer element 34, such as by interspersing the flows 24, 32 as the flows 24, 32 exit the outlet 44.

In one aspect of the invention, the mixer element 34 is configured as a heat exchanger to promote heating of the oxidizer flow 24 by absorbing a portion of the heat produced by oxidation in the partially oxidized mixture flow 32. For example, the respective flows 24, 32 have sufficient length along a direction of flow so that the temperature of the oxidizer flow 24 while flowing through the mixer element 34 is increased by a minimum of 100 degrees Fahrenheit. In an embodiment, the mixer element is configured to equilibrate the respective temperatures of the oxidizer flow 24 and the partially oxidized mixture flow 32 so that as the respective flows 24, 32 exit the mixer element 34, the respective flows 24, 32 have approximately the same temperature.

In another aspect, the mixer element 34 is configured to control the amount of heat exchange between the oxidizer flow 24 and the partially oxidized mixture flow 32. For example, the lengths of the respective flows 24, 32 in the mixer element 34 along a direction of flow are limited so that the temperature of the oxidizer flow 24 while flowing through the mixer element 34 is only increased by a maximum of 100 degrees Fahrenheit.

In a further aspect of the invention, the mixer element 34 may include tubes for containing a fluid flow. The oxidizer flow 24 may be directed to travel within the interior of the tubes, while the partially oxidized mixture flow 32 may be directed to travel around the exterior of the tubes. For example, the mixer element 34 may be configured as a tube/shell heat exchanger having a number of tubes housed within a shell, the tubes arranged in an interspersed manner within the shell to promote heat exchange between a fluid flow in the tubes and a different fluid flow in the shell directed to flow around the exterior of the tubes. For example, the oxidizer flow 24 may be directed to travel within the interiors of the tubes, while the partially oxidized mixture flow 32 may be directed to flow within the shell and around the exterior of the tubes. In addition, other methods may be used to separate the oxidizer flow 24 and the partially oxidized mixture flow 32, such as plates dividing the respective flows 24, 32.

In an embodiment, a baffle 40 may be disposed in one or both of the flows 24, 32 to ensure that the flow is evenly distributed throughout the mixer element 34. In another aspect of the invention, a mixer element retainer 42, such as a tubesheet, may be positioned at the outlet 44 of the mixer element 34 for providing improved mixing at the outlet 44.

After the flows 24, 32 exit the mixer element 34 at the outlet 44, the flows 24, 32 are mixed in a mixing chamber 46, to produce a hot combustible gas mixture 47. In the mixing chamber 46, interspersed mixing of the flows 24, 32 is the dominant process, while some combustion of the flows 24, 32 may occur. The hot combustible gas mixture 47 then passes into a secondary combustion chamber 48 to produce a hot combustion gas 49. In the secondary combustion chamber 48, the dominant process is combustion of the hot combustible gas mixture 47, while some mixing of the flows may continue. In some embodiments, the mixing chamber 46 and the secondary combustion chamber 48 may be combined in a single chamber. In an aspect of the invention, the single chamber may include a mixing zone and a combustion zone. In yet another embodiment, the secondary combustion chamber 48 may include an igniter.

A turbine 50 receives the hot combustion gas 49, where it is expanded to extract mechanical shaft power. In one embodiment, a common shaft 52 interconnects the turbine 50 with the compressor 12, as well as an electrical generator (not shown) to provide mechanical power for compressing the ambient air 14 and for producing electrical power, respectively. The expanded combustion gas 54 may be exhausted directly to the atmosphere or it may be routed through additional heat recovery systems (not shown).

Figure 2:
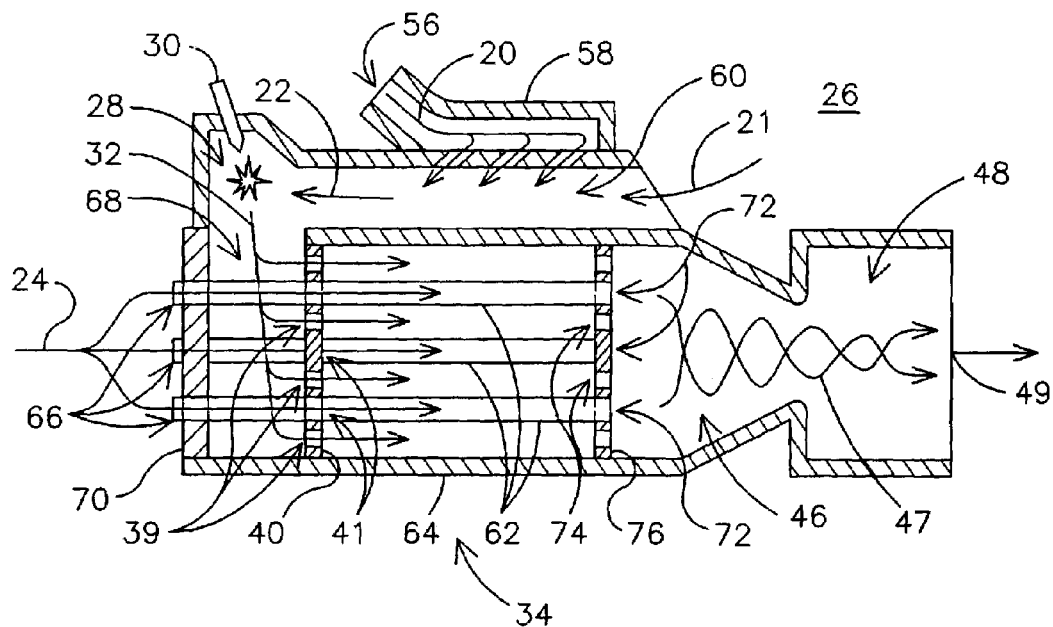
FIG. 2 illustrates a cross section of a combustor taken perpendicular to the direction of flow through the combustor.
Figure 3:
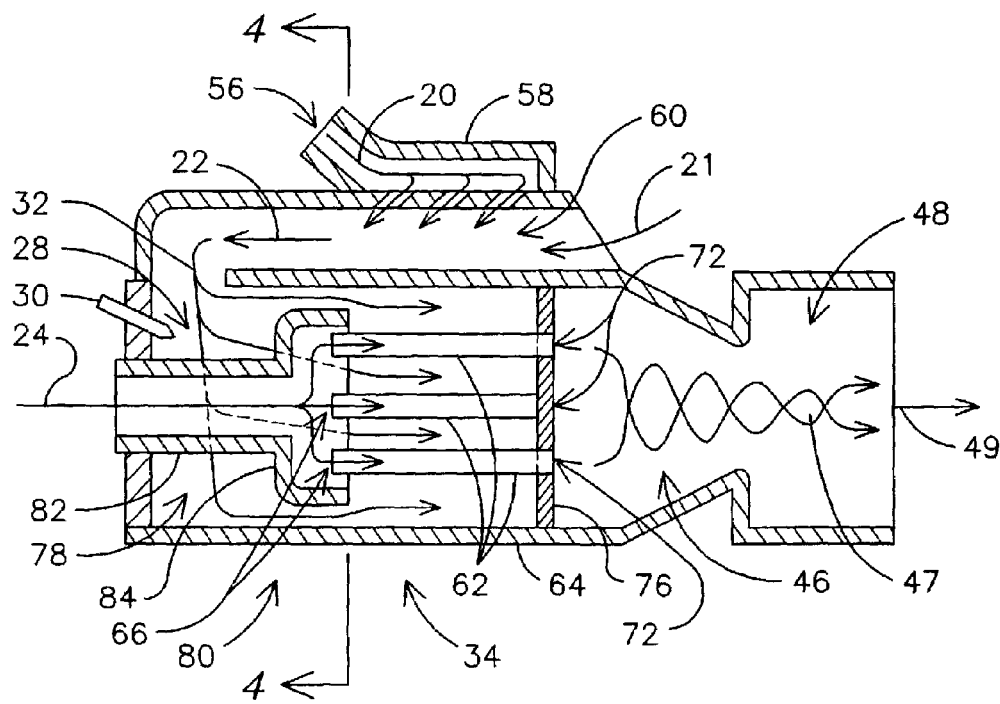
FIG. 3 illustrates a cross section of a combustor, including a manifold, taken perpendicular to the direction of flow through the combustor.

The combustor 26, as illustrated in the embodiments depicted in FIGS. 2 and 3, provides improved performance over prior catalytic or RQL combustion techniques by combining stabilization and, in one aspect, subsequent cooling, of a rich homogenous premixed flame with improved mixing of the partially combusted rich mixture with an oxidizer, such as bulk compressed air, for leaning the mixture after cooling. Accordingly, the combustor 26 eliminates the need for using a catalyst to decrease NOx emissions, while allowing increased product gas temperature for more stable downstream burning and better conversion efficiency than is possible using a catalytic technique. In addition, the mixer element 34 of the combustor 26 improves mixing of the oxidizer and the partially oxidized mixture and avoids high temperature, quasi-diffusion zone flames associated with typical RQL techniques.

In one embodiment, 12–18% by volume of the compressed air 16 provided by the compressor 12 is separated and mixed with fuel 20 to create the fuel-oxidizer mixture flow 22, which is then directed into the primary combustion chamber 28. In an aspect of the invention, the fuel to air ratio of the fuel-oxidizer mixture flow 22 has an equivalence ratio of between approximately 3–3.5. The fuel-oxidizer mixture flow 22 is partially combusted (for example, by igniting the mixture using the igniter 30) in the combustion chamber 28, creating a fuel-oxidizer mixture at or near its adiabatic flame temperature of 1500–1800 degrees Fahrenheit, and converting approximately 40% of the available carbon to carbon monoxide (CO). The resulting partially oxidized mixture flow 32 is then discharged into the partially oxidized mixture flow channel 36 of the mixer element 34. The remaining compressed air 16 (82–88% by volume) is directed into the oxidizer flow channel 38 of the mixer element 34. The mixer element 34 separates the partially oxidized mixture flow 32 from the oxidizer flow 24 as the respective flows 24, 32 move through the respective flow channels 36, 38. In an aspect of the invention, heat exchange between the flows 24, 32 is promoted within the mixer element 34 so that the oxidizer flow 24 absorbs heat from the partially oxidized mixture flow 32 in the combustion chamber 28. Accordingly, as the respective flows 24, 32 exit the mixer element 34 and mix in the mixing chamber 46, the temperature of the partially combusted flow 32 has been cooled to approximately 1100 degrees Fahrenheit. Advantageously, fuel conversion of the hot combustible gas mixture 47 as the gas 47 exits the mixing chamber 46 and is combusted in the secondary combustion chamber 48 is between approximately 75–90%. As a result, by promoting heat exchange to cool the partially oxidized mixture flow 32, a higher temperature partial combustion of the fuel-oxidizer mixture flow 22 can be maintained in the primary combustion chamber 28, resulting in a higher temperature, more stably burning, hot combustible gas mixture 47. In addition, a higher temperature partial combustion of the fuel-oxidizer mixture flow 22 in the primary combustion chamber 28 produces combustion products comprising mostly CO (40% available carbon to CO conversion) and $H_2$ (approximately 2 moles $H_2$ per mole of CO) that burn more stably to create the hot combustion gas 49.

While increasing partial combustion temperatures in conventional RCL type combustors can cause the catalyst to be burned off too quickly or destroy the catalyst, the invention allows higher partial combustion temperatures to be used. Accordingly, in another embodiment, an even higher primary adiabatic flame temperature in the primary combustion chamber 28 can be used to provide improved efficiency and reduced NOx emissions. For example, approximately 20% by volume of the compressed air 16 provided by the compressor 12 can be separated and mixed with the fuel 20 to create leaner fuel-oxidizer mixture flow 22. The fuel to air ratio of the resulting fuel-oxidizer mixture flow 22 provided to the combustion chamber 28 has an equivalence ratio of approximately 2.1. The fuel-oxidizer mixture flow 22 is partially combusted (for example, by igniting the mixture using the igniter 30) in the combustion chamber 28, creating an adiabatic flame temperature of 2580–2650 Fahrenheit, and approximately 80% of the available carbon is converted to CO. The resulting partially oxidized mixture flow 32 is then discharged into the partially oxidized mixture flow channel 36 of a mixer element 34. The remaining compressed air 16 (80% by volume) is directed into the oxidizer flow channel 38 of the mixer element 34 so that the mixer element 34 separates the partially oxidized mixture flow 32 from the oxidizer flow 24 as the respective flows 24, 32 move through the respective flow channels 36, 38. In an aspect of the invention, heat exchange between the flows 24, 32 is promoted by the mixer element 34 so that the oxidizer flow 24 absorbs a portion of the heat produced by partial combustion of the partially oxidized mixture flow 32 in the combustion chamber 28. Accordingly, as the respective flows 24, 32 exit the mixer element and mix to form the hot combustion gas 47 in the mixing chamber 46, the temperature of the resulting hot combustion gas 47 is approximately 1300 degrees Fahrenheit. Advantageously, fuel conversion of the hot combustion gas 47 as the gas 47 exits the mixing chamber 46 and is combusted in the secondary combustion chamber 48 is approximately 100%. The higher temperature partial combustion of the fuel-oxidizer mixture flow 22 in the primary combustion chamber 28 produces combustion products comprising mostly CO (80% available carbon to CO conversion) and $H_2$ (approximately 1.5 moles $H_2$ per mole of CO) that burn more stably to create the hot combustion gas 49.

In yet another embodiment of the invention, approximately 26% by volume of the compressed air 16 provided by the compressor 12 can be separated and mixed with fuel 20 to create the fuel-oxidizer mixture flow 22. The fuel to air ratio of the fuel-oxidizer mixture flow 22 provided to the combustion chamber 28 has an equivalence ratio of approximately 1.7. The fuel-oxidizer mixture flow 22 is partially combusted in the combustion chamber 28, creating an adiabatic flame temperature of approximately 3000 degrees Fahrenheit, and approximately 80% of the available carbon is converted to CO. The resulting partially oxidized mixture flow 32 is then discharged into the partially oxidized mixture flow channel 36 of the mixer element 34. Although some NOx precursors might be formed at a combustion temperature of 3000 degrees Fahrenheit, the creation of NOx precursors can be substantially reduced by making the heat release zone coincident with the heat exchange zone, such as by including the primary combustion chamber 28 within the mixer element 34. For example, an igniter 30 could be provided near an upstream end of the mixer element 34. In addition, bluff bodies could be positioned within the partially oxidized mixture flow channel 36 of the mixer element 34 to promote mixing of the partially oxidized mixture flow 32. In another aspect, an annular injector arrangement may be incorporated around the mixer element 34 to direct at least a portion of the partially oxidized mixture flow 32 into the mixer element 34 at distributed locations to promote mixing and flame stabilization within the mixer element 34.

The remaining compressed air 16 (74% by volume) is directed into the oxidizer flow channel 38 of the mixer element 34, separating the partially oxidized mixture flow 32 from the oxidizer flow 24 as the respective flows 24, 32 move through the respective flow channels 36, 38. In an aspect of the invention, heat exchange between the flows 24, 32 is promoted by the mixer element 34 so that the oxidizer flow 24 absorbs a portion of the heat produced by partial combustion of the partially oxidized mixture flow 32 in the combustion chamber 28. Accordingly, as the respective flows 24, 32 exit the mixer element and mix to form hot combustible gas mixture 47 in the mixing chamber 46, the temperature of the gas 28 is approximately 1500 degrees Fahrenheit. Advantageously, fuel conversion of the hot combustible gas mixture 47 as the gas 47 exits the mixing chamber 46 and is combusted in the secondary combustion chamber 48 is approximately 100%. The higher temperature partial combustion of the fuel-oxidizer mixture flow 22 in the primary combustion chamber 28 produces combustion products comprising mostly CO (80% available carbon to CO conversion) and $H_2$ (approximately 1.1 moles $H_2$ per mole of CO) that burn stably to create the hot combustion gas 49.

It should be noted that the specific percentages of inlet air used and the resulting equivalency ratios cited in the above embodiments are intended as examples only. Equivalency ratios of the fuel-oxidizer mix used in the invention may range from approximately 1.7 to 3.5, while the percentage, by volume, of compressed air 16 directed into the primary combustion chamber 28 may range from approximately 12% to 26%. In addition, overall equivalency ratios (based on the amount, by volumes, of fuel 20 supplied and total compressed air 16 supplied to the combustor) of between approximately and 0.4 to 0.55 may be used.

FIG. 2 illustrates a cross section of an embodiment of the combustor 26 of FIG. 1 taken perpendicular to the direction of flows 24,32 through the combustor 26. The combustor 26 includes a primary combustion chamber 28, a mixer element 34, and a secondary combustion chamber 48. The flow of combustible fuel 20 is introduced into the combustor 26 at a fuel inlet 56 of a fuel manifold 58. The fuel mixing oxidizer flow 21 is introduced into a fuel premixing chamber 60 to allow premixing of the fuel mixing oxidizer flow 21 with the flow of combustible fuel 20 to create a fuel oxidizer mixture flow 22. The fuel oxidizer mixture flow 22 is received in the primary combustion chamber 28, where the fuel oxidizer mixture flow 22 is partially combusted into a partially oxidized mixture flow 32. For example, the oxidizer mixture flow 22 may be ignited by an igniter 30 positioned in the primary combustion chamber 28 to initiate combustion. In an aspect of the invention, the primary combustion chamber 28 extends annularly around the combustor 26 at an upstream end. The partially oxidized mixture flow 32 is then discharged into the mixer element 34. The oxidizer flow 24 is directed into the mixer element 34, so that the mixer element 34 separates the partially oxidized mixture flow 32 from the oxidizer flow 24 as the respective flows 24, 32 move through the mixer element 34.

In an aspect of the invention, the mixer element 34 can be configured as a tube/shell heat exchanger, wherein the tubes 62 form the flow channels 38 for the oxidizer flow 24 and separate the oxidizer flow 24 from the partially oxidized mixture flow 32. The sidewall 64 of the combustor 26 portion defining the mixer element 34 forms the shell of the heat exchanger and directs the partially oxidized mixture flow 32 around the tubes 62 in the mixer element 34 to promote heat exchange. Accordingly, the oxidizer flow 24 is directed into the tube inlets 66, while the partially oxidized mixture flow 32 discharged from the primary combustion chamber 28 is directed into an inlet end 68 of the mixer element 34. In another aspect, a baffle plate 40, allowing the tubes 62 and the partially oxidized mixture flow 32 to pass through, may be provided near the partially oxidized mixture flow inlet 68 to distribute the partially oxidized mixture flow 32 around all the tubes 62 in the mixer element 34. For example, the baffle plate 40 may have tube passageways 41 to allow passage of the tubes 66 therethrough, and flow passageways 39, positioned and sized to equally distribute, in a two-dimensional manner, the partially oxidized mixture flow 32 therethrough. In another aspect, an upstream tubesheet 70 may be provided to retain the tubes 62 near the tube inlets 66.

The oxidizer flow 24 travels in the interior of the tubes 62, while the partially oxidized mixture flow 32 travels around the exterior of the tubes 62, heating the oxidizer flow 24 as the respective flows 24, 32 pass through the mixer element 34. In another aspect of the invention, the length of the tubes 62 can be limited so that heat exchange between the respective flows 24, 32 is minimized. As a result, the mixer element's 34 primary function in a limited length configuration is to promote improved mixing of the flows 24, 32 downstream of the mixer element 34.

At a downstream end of the mixer element 34, tube outlets 72 are interspersed among partially oxidized mixture flow outlets 74 to promote distributed mixing of the respective flows 26, 32 exiting the mixer element 34. For example, a downstream tubesheet 76 may be provided to retain the tubes 62 near the tube outlet 72, and allow the respective flows 26, 32 to pass through in an interspersed manner, so that distributed mixing of the flows 26, 32 is enhanced. Accordingly, the interspersed flows 26, 32 are discharged from the mixer element 34 into the mixing chamber 46 to form a well-mixed hot combustible gas mixture 47, that can be further combusted in the secondary combustion chamber 48 to create a hot combustion gas 49 for introduction into the downstream turbine 50.

FIG. 2 is an example of the process concept. Alternatives, such as having the reactive mixture on the inside of the tubes and the coolant on the outside, or using flat plates to separate rectangular channels containing alternating reactive mixture and cooling air, are apparent to those skilled in the art without departing from this invention.

FIG. 3 illustrates a cross section of a combustor 26, including a manifold 78, taken perpendicular to the direction of flows 24,32 through the combustor 26. The combustor 26 comprises a primary combustion chamber 28, a manifold 78, a mixer element 34, and a secondary combustion chamber 48. In the embodiment depicted in FIG. 3, the combustion chamber extends into a body 80 of the combustor 26. The flow of combustible fuel 20 is introduced into the combustor 26 at the fuel inlet 56 of the fuel manifold 58. The fuel mixing oxidizer flow 21 is then directed into the fuel premixing chamber 60 to allow premixing of the fuel mixing oxidizer flow 21 with the flow of combustible fuel 20 to create the fuel oxidizer mixture flow 22. The fuel oxidizer mixture flow 22 is received in the primary combustion chamber 28, where the fuel oxidizer mixture flow 22 is combusted into a partially oxidized mixture flow 32. For example, the oxidizer mixture flow 22 may be initially ignited by an igniter 30 positioned in the primary combustion chamber 28 to partially combust the fuel oxidizer mixture flow 22. In a further aspect, the primary combustion chamber 28 may include structure to stabilize combustion, such as providing recirculation zones within the primary combustion chamber 28 to return hot combustion products to an ignition zone, such as near the igniter 30 to ignite the mixture. For example, swirling structures, such as vanes appropriately positioned in the primary combustion chamber 28, or step expansion features included in the primary combustion chamber 28, may be incorporated to improve flame stability.

From the primary combustion chamber 28, the partially oxidized mixture flow 32 is discharged into the mixer element 34. The oxidizer flow 24 can be directed by the manifold 78 into the mixer element 34, so that the mixer element 34 separates the partially oxidized mixture flow 32 from the oxidizer flow 24 as the respective flows 24, 32 move through the mixer element 34.

In an embodiment, the mixer element 34 includes a number of tubes 62 forming the oxidizer flow channels 38, confining the oxidizer flow 24 and separating the oxidizer flow 24 from the partially oxidized mixture flow 32. In an aspect of the invention, a manifold 78 distributes the oxidizer flow 24 among the tubes 62. The manifold 78 may include an elongated portion 82 at an upstream end for passing the oxidizer flow 24 through the primary combustion chamber 28, and a distributing portion 84 at a downstream end, for mounting the respective tube inlets 66 of the tubes in fluid communication with manifold 78 and directing the oxidizer flow 24 in the elongated portion 82 into the tube inlets 66. The manifold 78 defines an upstream end of the mixer element 34 and can be configured to allow passage of the partially oxidized mixture flow 32 around the exterior of the manifold 78 into the mixer element 34. For example, as shown in the sectional view FIG. 4, the distributing portion 84 of the manifold 78 may include a number of arms 86 for dividing and directing the oxidizer flow 24 into respective tube inlets 66, wherein the spaces between the arms 86 allow the partially oxidized mixture flow 32 to pass around the distributing portion 84 and into the mixer element 34. Although a generally rectangular configuration is depicted in FIG. 4, any number of configurations could be used by those skilled in the art to match the interior shape of the combustor while directing the oxidizer flow 24 into respective tubes 66 and allowing the partially oxidized mixture flow 32 to pass around the manifold 78 and into the mixing chamber 34.

After the partially oxidized mixture flow 32 enters the mixer element 34 from the primary combustion chamber 28, the sidewall 64 of the combustor 26 portion defining the mixer element 34 confines the partially oxidized mixture flow 32 to flow around the tubes 62. In an embodiment, the length of the tubes 62 can be limited so that heat exchange between the respective flows 24, 32 is minimized. As a result, the mixer element's 34 primary function in a limited length configuration is to promote improved mixing of the flows 24, 32 downstream of the mixer element 34.

At a downstream end of the mixer element 34, tube outlets 72 are interspersed among partially oxidized mixture flow outlets 74 to promote distributed mixing of the respective flows 24, 32 exiting the mixer element 34. For example, a downstream tubesheet 76 may be provided to retain the tubes 62 near the tube outlet 72 and allow the respective flows 24, 32 to pass through in an interspersed manner so that distributed mixing of the flows 24, 32 is enhanced. Accordingly, the interspersed flows 24, 32 are discharged from the mixer element 34 into the mixing 46 to form a well-mixed combustible gas mixture 47, that can be further combusted in the secondary combustion chamber 48 to create a hot combustion gas 49 for introduction into the downstream turbine 50.

FIG. 3 is an example of the process concept. Alternatives, such as having the reactive mixture on the inside of the tubes and the coolant on the outside, or using flat plates to separate rectangular channels containing alternating reactive mixture and cooling air, are apparent to those skilled in the art without departing from this invention.

While the preferred embodiments of the present invention have been shown and described herein, it will be obvious that such embodiments are provided by way of example only. Numerous variations, changes and substitutions will occur to those of skill in the art without departing from the invention herein. For example, the combustor 26 may include a start up pilot positioned proximate the secondary combustion chamber 48, such as a central pilot in a can annular configuration of combustors 26. Accordingly, it is intended that the invention be limited only by the spirit and scope of the appended claims.

We claim as our invention:

1. A combustor comprising:
   a primary combustion chamber receiving a first fuel-oxidizer mixture and discharging a partially oxidized mixture;
   a mixer element receiving the partially oxidized mixture and a flow of an oxidizer into a plurality of separate flow channels and comprising a plurality of outlet ends discharging the partially oxidized mixture interspersed among a plurality of outlet ends discharging the oxidizer;
   a chamber in fluid communication with the outlet ends of the mixer element for mixing the partially oxidized mixture with the oxidizer downstream of the mixer element; and
   further comprising a secondary combustion chamber for further combusting the partially oxidized mixture with the oxidizer downstream of the chamber.

2. The combustor of claim 1, wherein the mixer element comprises a heat exchanger.

3. The combustor of claim 2, wherein the mixer element comprises a tube/shell heat exchanger.

4. A combustor comprising:
   a primary combustion chamber receiving a first fuel-oxidizer mixture and discharging a partially oxidized mixture;
   a mixer element receiving the partially oxidized mixture and a flow of an oxidizer into a plurality of separate flow channels and comprising a plurality of outlet ends discharging the partially oxidized mixture interspersed among a plurality of outlet ends discharging the oxidizer;
   a chamber in fluid communication with the outlet ends of the mixer element for mixing the partially oxidized mixture with the oxidizer downstream of the mixer element;
   wherein the mixer element comprises a heat exchanger; and
   wherein the mixer element flow channels have sufficient respective lengths along a direction of flow so that a temperature of the oxidizer is increased by a minimum of 100 degrees Fahrenheit across the mixer element.

5. A combustor comprising:
   a primary combustion chamber receiving a first fuel-oxidizer mixture and discharging a partially oxidized mixture;
   a mixer element receiving the partially oxidized mixture and a flow of an oxidizer into a plurality of separate flow channels and comprising a plurality of outlet ends discharging the partially oxidized mixture interspersed among a plurality of outlet ends discharging the oxidizer;
   a chamber in fluid communication with the outlet ends of the mixer element for mixing the partially oxidized mixture with the oxidizer downstream of the mixer element; and
   wherein the mixer element flow channels have respective lengths along a direction of flow so that a temperature of the oxidizer is increased by a maximum of 100 degrees Fahrenheit across the mixer element.

6. The combustor of claim 1, wherein the mixer element comprises a plurality of tubes.

7. The combustor of claim 6, wherein the mixer element further comprises a tubesheet at a downstream end of the tubes for allowing passage of the partially oxidized mixture and the oxidizer into the chamber.

8. The combustor of claim 6, further comprising a tubesheet at an upstream end of the tubes.

9. The combustor of claim 1, further comprising an igniter positioned in the primary combustion chamber.

10. The combustor of claim 1, wherein the mixer element further comprises a baffle plate disposed upstream of the respective outlet ends of the mixer element proximate a primary combustion chamber outlet end and configured to allow passage of the oxidizer and the partially oxidized mixture therethrough.

11. The combustor of claim 1, wherein the mixer element further comprises a manifold dividing the oxidizer into a plurality of oxidizer fluid flows.

12. The combustor of claim 1, wherein the first fuel-oxidizer mixture has an equivalence ratio of between approximately 1 and 3.5.

13. The combustor of claim 1, wherein the partially oxidized mixture has an adiabatic flame temperature of between approximately 1500 degrees Fahrenheit and 3000 degrees Fahrenheit in the primary combustion chamber.

14. A gas turbine engine comprising the combustor of claim 1.

15. A combustor for a gas turbine engine comprising:
a primary combustion chamber receiving a first fuel-oxidizer mixture and discharging a partially oxidized mixture;
a mixer element receiving the partially oxidized mixture and a flow of an oxidizer into a plurality of separate flow channels, wherein the mixer element comprises a heat exchanger comprising a shell for receiving the partially oxidized mixture, a plurality of tubes for receiving the flow of the oxidizer, and a plurality of outlet ends discharging the partially oxidized mixture interspersed among the plurality of outlet ends discharging the oxidizer;
a chamber in fluid communication with the outlet ends of the mixer element for mixing the partially oxidized mixture with the oxidizer downstream of the mixer element; and
a secondary combustion chamber for further combusting the partially oxidized mixture with the oxidizer downstream of the mixing chamber.

16. The combustor of claim 15, further comprising a tubesheet at a downstream end of the tubes.

17. The combustor of claim 15, further comprising a tubesheet at an upstream end of the tubes.

18. The combustor of claim 15, further comprising a baffle plate, disposed upstream of the respective outlet ends of the heat exchanger proximate a primary combustion chamber outlet end.

* * * * *